United States Patent [19]

Familletti

[11] Patent Number: 5,081,036
[45] Date of Patent: Jan. 14, 1992

[54] METHOD AND APPARATUS FOR CELL CULTURE

[75] Inventor: Philip C. Familletti, Millington, N.J.

[73] Assignee: Hoffmann-La Roche Inc., Nutley, N.J.

[21] Appl. No.: 590,317

[22] Filed: Sep. 28, 1990

Related U.S. Application Data

[63] Continuation of Ser. No. 490,528, Mar. 5, 1990, abandoned, which is a continuation of Ser. No. 7,072, Jan. 23, 1987, abandoned.

[51] Int. Cl.$^5$ ............................................. C12M 3/02
[52] U.S. Cl. ............................. 435/286; 435/240.23; 435/240.243; 435/287; 435/289; 435/290; 435/299; 435/313; 435/316
[58] Field of Search .................... 435/240.23, 240.243, 435/287, 289, 290, 299, 313, 316, 286

[56] References Cited

U.S. PATENT DOCUMENTS

| | | |
|---|---|---|
| 3,649,465 | 3/1972 | Scharf et al. |
| 3,726,597 | 4/1973 | Dvorak et al. |
| 3,976,547 | 8/1976 | McAleer et al. |
| 4,036,693 | 7/1977 | Levine et al. |
| 4,085,007 | 4/1978 | Hawkins |
| 4,133,644 | 1/1979 | Holloway et al. .................. 422/138 |
| 4,173,516 | 11/1979 | Katinger et al. |
| 4,204,042 | 5/1980 | Chelle |
| 4,208,483 | 6/1980 | Lee |
| 4,259,449 | 3/1981 | Katinger et al. |
| 4,311,798 | 1/1982 | Katinger et al. |
| 4,337,315 | 6/1982 | Fukushima |
| 4,545,945 | 10/1985 | Prave et al. |
| 4,649,117 | 3/1987 | Familletti ...................... 435/240.24 |

FOREIGN PATENT DOCUMENTS

| | | |
|---|---|---|
| 01126A | 9/1986 | Denmark |
| 194401 | 9/1986 | European Pat. Off. |
| 1426975 | 12/1965 | France |
| 2133355 | 10/1972 | France |
| 0179495 | 10/1983 | Japan |
| 05630 | 12/1985 | PCT Int'l Appl. |

OTHER PUBLICATIONS

Feder et al., The Large-Scale Cultivation of Mammalian Cells, (1983, pp. 36-43, Scientific American 248, No. 1.
Onken et al., Airlift Fermenters: Construction, Behaviour and Uses, (1983), pp. 67-95, Advances in Biotechnological Processes 1.
The Bellco Bioreactor-A New Standard for Cell Culture Productivity Convenience and Control; (9/1985).
Webb et al., "The Product of Cellulase in a Spouted Bed Fermentor Using Cells Immobilized in Biomass Support Particles", 6034 Biotechnology & Bioengineering 28 pp. 41-50, (1986).

Primary Examiner—Robert J. Warden
Assistant Examiner—Timothy M. McMahon
Attorney, Agent, or Firm—George M. Gould; Bernard S. Leon; George W. Johnston

[57] ABSTRACT

Methods and apparatus are provided for growing both suspension type cells and anchorage dependent cells in airlift bioreactors. A packing means, such as stainless steel wool, is provided in the growth chamber of the bioreactor to increase cell density by trapping suspension cells or acting as a solid support for anchorage depended cells without interfering with gentle circulation of liquid growth medium in the bioreactor.

9 Claims, 2 Drawing Sheets

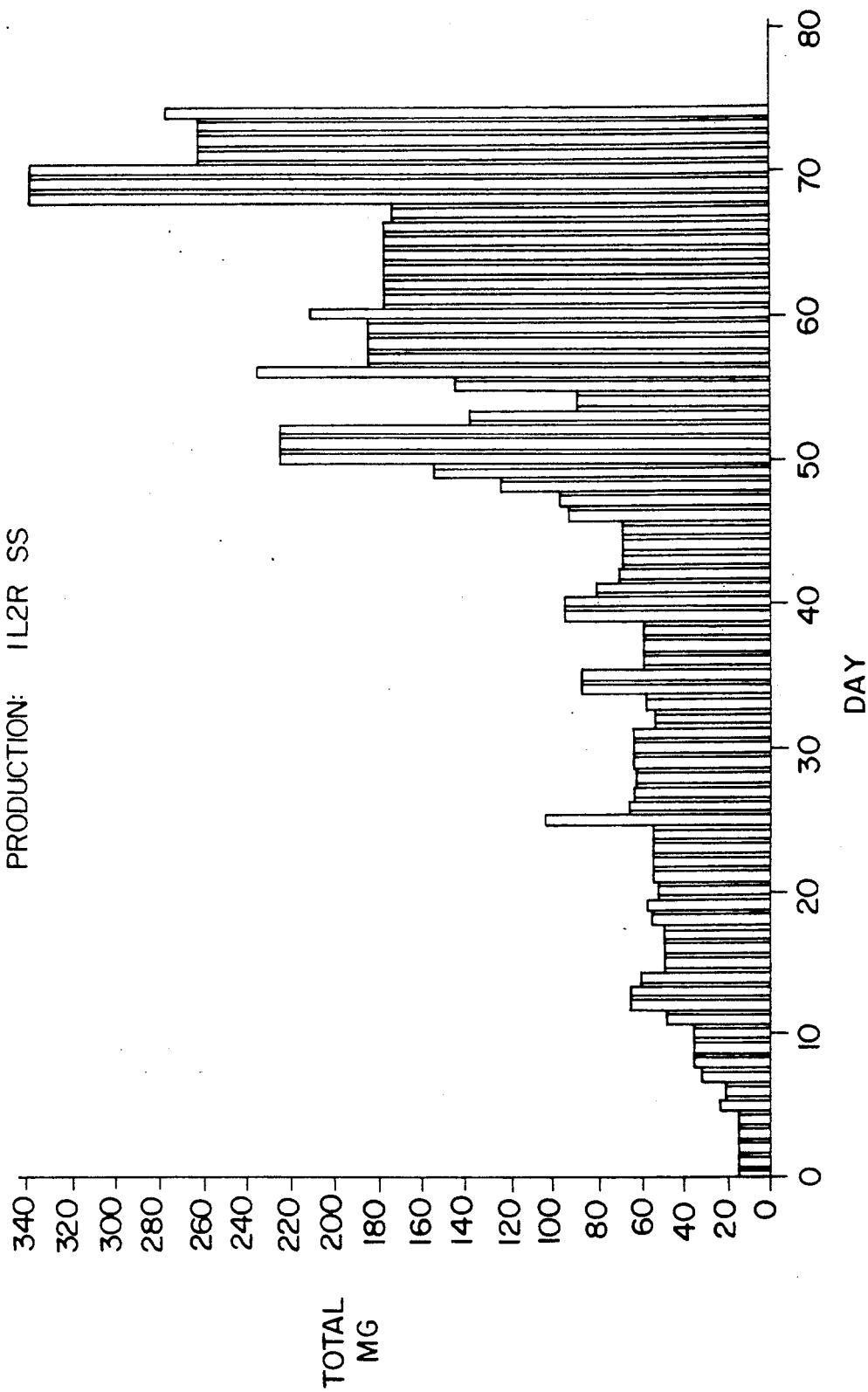

5,081,036

METHOD AND APPARATUS FOR CELL CULTURE

This application is a continuation of application Ser. No. 07/490,528, filed Mar. 5, 1990, now abandoned, which is a continuation of application Ser. No. 077/007,072, filed Jan. 23, 1987, now abandoned.

FIELD OF THE INVENTION

This invention relates to airlift bioreactors which include a solid support material to facilitate cell culture as well as methods of operating same.

BACKGROUND OF THE INVENTION

Various types of airlift bioreactors are known. See for example, "Airlift Fermenters: Construction Behavior and Uses". Advances in Biotechnology Processes I, pages 67-95, 1983, Alan R. Liss, New York. N.Y.

A particular commercially available airlift bioreactor which can be readily modified according to the present invention has an upper growth chamber which is connected to a lower smaller diameter mixing chamber via a downwardly and inwardly sloping conical section. A gas mixture is sparged into the mixing chamber and sets up a gentle circulation of liquid growth medium within the growth chamber.

Certain cell lines are anchorage dependent as is well known in the art. This means that the cells must be grown in an environment wherein they can be attached to a solid support material. Heretofore, this has been accomplished, for example, by attaching the cells to stacked petrie dishes or by growing the cells in roller bottles. Each of these approaches has drawbacks such as the inability to achieve high volumetric cell density or inadequate circulation of nutrients, etc. necessary to growth of the cells.

Another known method of growing anchorage dependent cells uses gel bead immobilization. Using this technique, the cells are immobilized within small beads formed from alginate gel, for example. The cell containing beads may be suspended in a liquid growth medium and just like suspension type cells may be circulated to provide adequate contact with nutrients and dissolved gases to promote cell growth.

SUMMARY OF THE INVENTION

According to the invention, airlift bioreactors are improved by including a packing material in their growth chambers for increasing cell density, providing a solid support for anchorage dependent cells and increasing gas dissolution into liquid growth medium circulating within the growth chamber.

Additionally, the invention provides methods of growing cells in airlift bioreactors having growth chambers which include a packing material. These methods relate to the growing of suspension cells as well as anchorage dependent cells.

BRIEF DESCRIPTION OF THE DRAWINGS

FIG. 2 is a graph showing daily production of receptor protein using the bioreactor shown in FIG. 1.

DESCRIPTION OF THE PREFERRED EMBODIMENT

Figure 1:
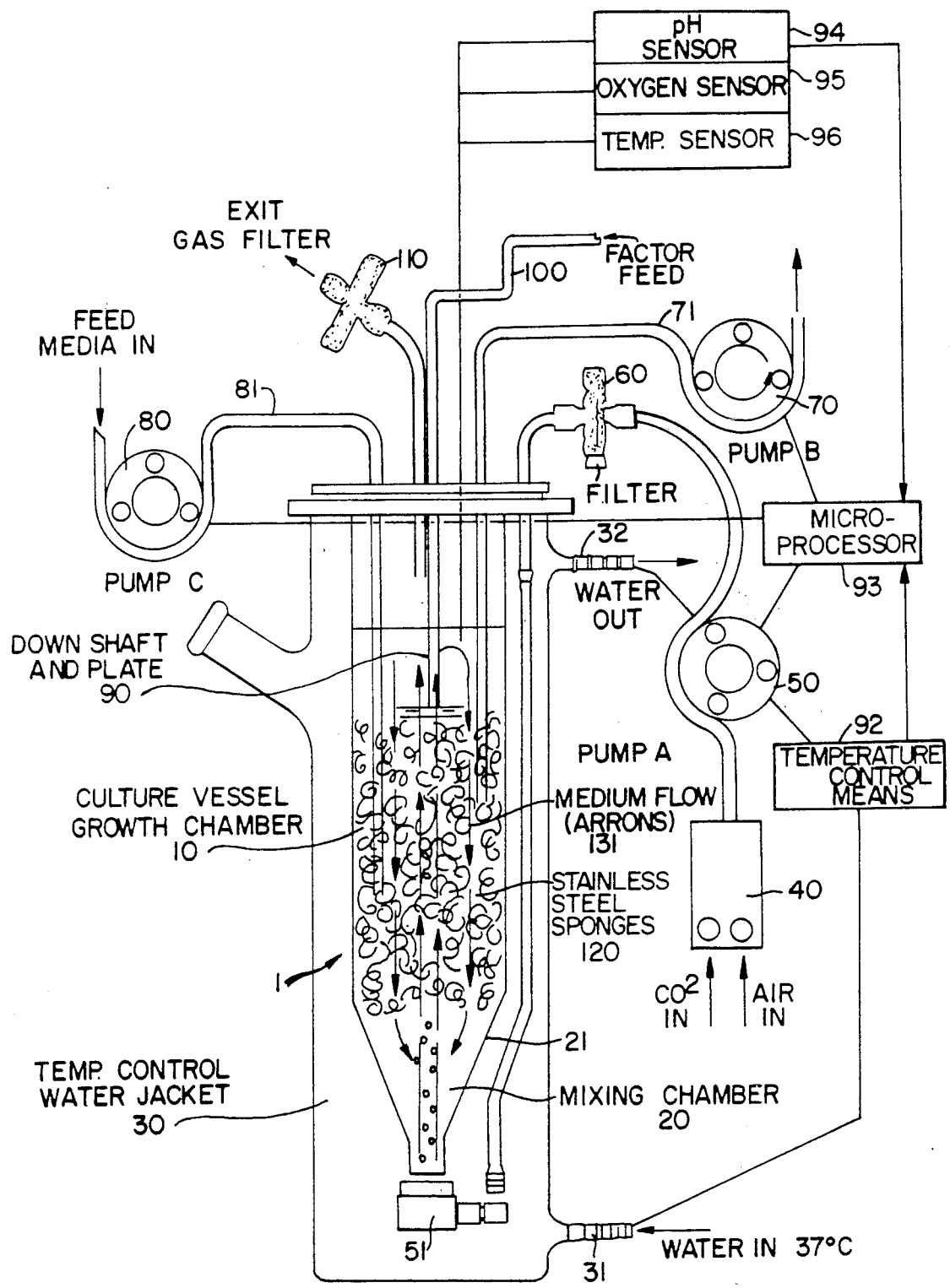
FIG. 1 shows an airlift bioreactor having a stainless steel solid support material in its growth chamber according to a preferred embodiment of the invention.

As used herein the term "anchorage dependent cells" shall refer to any cells particularly mammalian, which will grow and multiply when attached to a solid support material and shall include but are not limited to cells which will only grow when attached to a solid support material. Examples of anchorage dependent cells which may be grown using the apparatus and methods according to the invention include but are not limited to Chinese Hamster Ovary cells, ATTC No. CCL-61.

The term "liquid growth medium" shall refer to any liquid medium in which cells may be grown. A particularly preferred growth medium for use in growing mammalian cells according to the present invention is Iscove's modified Dulbecco's medium supplemented with heat inactivated fetal calf serum.

The term "packing material" shall refer to any material placed within an airlift bioreactor which can serve as a solid support for the attachment of anchorage dependent cells and which will catch rising gas bubbles and suspended cells without totally disrupting gentle circulation of liquid growth medium within the bioreactor. Preferably, the packing material is finely divided into long thin strands, beads, etc. which imports a high surface area for a given volume. This finely divided state allows liquid growth medium to flow through the packing material and contact all the cells attached to it or trapped within it.

In this sense, cells grown in the bioreactor are essentially held stationary by the packing material while the liquid growth medium is in constant circulation.

Packing materials having a broad surface area such as extended baffles are unsuitable. Such large disruptions cause turbulence which necessitates higher driving forces to maintain circulation and also promote excessive foaming.

The ability of the packing material to catch gas bubbles is important because it increases the contact time between gas and the liquid growth medium which improves gas dissolution and thereby allows the bioreactor to support an increased cell density.

Suitable packing materials include but are not limited to long filament like materials such as stainless steel wool, fiber glass (glass wool), and polymer strands as well as small beads of glass or plastic such as polyethylene, collagen beads, polysaccharide beads such as alginate or hydroxymethy cellulose beads etc. as well as mixtures of any of these. A particularly preferred packing material is stainless steel wool.

A preferred airlift bioreactor systems for use in the present invention is shown in FIG. 1. The system includes a bioreactor 1 within a temperature control water jacket 30. The temperature control water jacket 30 has a water inlet 31 for receiving temperature controlled water from suitable temperature control means. In a preferred embodiment, the temperature control means 92 is connected to the water inlet 31 and the water outlet 32 as shown in FIG. 1. The temperature controlled water exits the temperature control jacket 30 via outlet 32. The temperature control jacket preferably maintains the bioreactor 1 at a preselected temperature suitable for cell growth.

The bioreactor 1 has from top to bottom a growth chamber 10 including packing means 120. The growth chamber 10 is connected via a downwardly and inwardly sloping conical section 21 to a mixing chamber 20 of smaller diameter than the growth chamber 10.

A preferred airlift bioreactor for use in the present invention is described in U.S. patent application Ser. No. 711,932, filed Mar. 15, 1985 now U.S. Pat. No. 4,649,117 the specification of which is incorporated herein by reference.

In operation the bioreactor 1 is filled with a liquid growth medium 130 suitable for culture of the particular cells to be grown.

First, cells to be grown in the bioreactor are introduced into the liquid growth medium 130. Then the liquid growth medium 130 is introduced into the bioreactor 1 by medium pump 80 via medium feed line 81 until the growth chamber 10 is partly filled.

Gas is then sparged up through the liquid growth medium 130 within the bioreactor 1 via gas sparger 51. The upwardly flowing gas constitutes a stream of gas bubbles which instigates a gentle circulation of liquid growth medium 130 within the bioreactor 1. This gentle circulation is denoted by arrows 131.

As can be seen, packing means 120 is positioned within bioreactor 1 so as to intersect at least a portion of the liquid growth medium 130 which is gently circulating within the bioreactor 1. Preferably, the packing means is positioned within the growth chamber 10 with no packing means being located in the conical section 21 or mixing chamber 20. Also, the liquid growth medium 130 is preferably filled to a level extending above the top of the packing means 120. To facilitate this, the packing means only extends part of the height of the growth chamber 10 and is held down by hold down means 90. Preferably, hold down means 90 is a shaft extending out through the top of the bioreactor having a lower end terminating in a plate atop the packing means 120 as shown. This hold down means in its preferred form is a hollow tube which provides a conduit into the bioreactor to which an external line, may be connected, such as factor feed line 100 as shown.

The gentle circulation of liquid growth medium and cells is continued to ensure homogeneity within the bioreactor. Then, if desired, the gentle circulation can be briefly discontinued (by stopping the sparging), for a period sufficient to allow anchorage dependent cells to adhere to the packing means 120.

In operation, factors such as glucose, various nutrients, and sodium hydroxide to control the pH, etc. may be introduced as needed into growth chamber 10 via the factor feed line 100.

From time to time or on a continuous basis spent liquid growth medium may be withdrawn from the bioreactor 1 via media harvest line 71 using pump 70 and replaced with fresh liquid growth medium via media feed line 81 and pump 80.

In the above manner, cells can be grown in the bioreactor, which cells are, transfected for example, with a particular human gene for producing a particular biological product (e.g., protein, enzyme, hormone, chimeric antibody, etc.) which the cells will release into liquid growth medium 130. In accordance with one aspect of the invention, this biological product is then recovered from the harvested liquid growth medium using known methods.

Preferably, the gas being introduced into the bioreactor 1 is a mixture of $CO_2$ and oxygen containing gas, such as air. Flow meter 40 is used to adjust in known manner the relative mixture of $CO_2$ to air in known manner based on the oxygen demand of the cells being grown as well as the pH of the liquid growth medium 130 within bioreactor 1 while the total flow rate of both gases is controlled by pump 50.

The bioreactor may contain various sensors, such as a pH sensor 94, and oxygen sensor 95 and a temperature sensor 96 for respectively measuring the pH, oxygen content and temperature of the liquid growth medium 130. Additionally, these sensors may be connected to a preprogrammable microprocessor 93. The microprocessor is preferably connected to pump 50, pump 70 and pump 80, for controlling the pumps in a known manner as illustrated in FIG. 1.

The invention will now be described with reference to the following example which is illustrative only and is not meant to limit the scope of the invention in any way. The example was performed as written.

EXAMPLE

Chinese Hamster Ovary (CHO) cell line, obtained from the ATTC. No. CCL-61 which were transfected with the human gene for the interlukin 2 (Il 2) receptor protein were grown in an airlift bioreactor according to the following procedure.

An airlift bioreactor obtained from Bellco Glass Inc., Vineland, N.J. was packed with six stainless steel sponges. The sponges were packed in such a way as to make a tight fit with the glass wall of the reactor. However, no sponges or parts thereof were in the mixing chamber of the reactor. The sponges were held securely in place with an adjustable shaft attached to the top of the reactor. The basic features of this bioreactor including the stainless steel sponges are as illustrated in FIG. 1.

Each of the stainless steel sponges was a "Kurly Kate" sanitary stainless steel sponge, #756 which was obtained from Purex Industrial, Lawrence, Mass. Each sponge was made up of numerous strands of stainless steel in a coiled spring like configuration. The strands were virtually continuous in length and measured approximately 0.016 inches in width and approximately 0.004 inches in thickness. The total surface area of a single sponge was calculated to be 3,396 square centimeters ($cm^2$). Each sponge was rinsed in distilled water prior to being packed in the reactor. The total surface area of all six sponges in the reactor was calculated to be 20,376 $cm^2$.

The reactor containing the sponges was then steam sterilized in an autoclave.

The liquid growth medium which was used was an Iscove's modified Dulbecco's medium, obtained from Gibco Laboratories #430-2200. It was supplemented with 2% heat inactivated fetal calf serum which was obtained from Kansas City Biological.

The CHO cells, were first grown in conventional roller bottles. Then some of these cells were suspended in the liquid growth medium using known procedures. This suspension of cells was then introduced into the sterile bioreactor. The liquid growth medium in the reactor was sparged at a rate of 50 cc-min for 5 minutes to obtain a homogeneous mixture of cells. The sparge was stopped for 45 minutes to facilitate attachment of the CHO cells to the stainless steel sponges. The sparge was then restarted.

The bioreactor was allowed to function continuously and held at a constant temperature of 37° C. The pH of the liquid growth medium, glucose consumption, lactate production and product (receptor protein) were monitored daily.

Periodically, spent medium containing receptor protein was removed from the bioreactor and replaced with fresh medium.

It was observed that cells attached readily to the stainless steel sponges. All cells appeared to become attached within the first half hour of incubation. The sponges acted as a substrate for the cells and also as a trap for air bubbles in the gas stream. This trapping action helped to increase dissolved oxygen in the culture medium.

A gentle circulation pattern of liquid growth medium occurred as shown in FIG. 1. not withstanding the positioning of the stainless steel sponges within the growth chamber. Thus the fluid dynamics of the bioreactor containing the stainless steel sponges was such as to create a homogeneous environment for the cells with respect to nutrients and dissolved oxygen.

The production rate of human receptor is shown in FIG. 2. Spent medium was collected and assayed in known manner by an ELISIA type assay for the presence of receptor protein. The bars in FIG. 2 represent the total amount of receptor protein harvested each day for the first 74 days of cell growth.

Production of I12 receptor ranged from 12.5 to 320 milligrams per day which an average daily production of approximately 120 milligrams. In contrast, daily production of receptor protein by CHO cells grown in a conventional 850 $cm^2$ roller bottle was found to be approximately 1.65 milligrams per day.

As can be seen from the forgoing example, the bioreactor apparatus incorporating the packing material according to the present invention is well suited to the growth of anchorage dependent cells such as the CHO cell line illustrated.

However, the apparatus of the present invention would also be suitable for the growth of suspension cells. Suspension cells would be trapped within the packing material much the same way air bubbles were trapped in the Example. In this way, the cell density of the suspension type cells within the bioreactor could be increased. Because the packing material does not impair the gentle circulation of liquid growth medium within the growth chamber, all cells which are located within the packing material are readily contacted with the circulating liquid growth medium containing nutrients and dissolved gases.

As mentioned previously another advantage of the use of packing material in an airlift bioreactor according to the invention is the entrapment of air bubbles within the packing material. This entrapment provides longer contact time between the air bubbles and the liquid growth medium gently circulating within the bioreactor and thereby permits more gas to be dissolved within the liquid growth medium at a given sparging rate. That is, a greater amount of gas may be dissolved within the liquid growth medium for supporting greater number of cells within the bioreactor without increasing the sparging rate beyond that which would provide a gentle circulation of liquid growth medium within the bioreactor. As it known in the art, sparging rates must be limited so as to avoid excessive amounts of foaming which might disrupt the operation of the bioreactor.

The foregoing description of the preferred embodiment has been provided for the purpose of illustrating the invention but is not meant to limit the scope thereof to the particular embodiments described.

I claim:

1. An airlift bioreactor for growing cells which release biological products in a liquid growth medium, said bioreactor comprising:
   a. a growth chamber for receiving the cells and the liquid growth medium and providing an environment for cell growth, said growth chamber having internal side walls which define a middle region;
   b. means for gently bubbling a stream of gas up through the middle region of said growth chamber to thereby cause gentle circulation of the liquid growth medium up through the middle region of said growth chamber and then back down along the internal side wall of said growth chamber; and
   c. stainless steel filament sponge located within said growth chamber to intersect at least a portion of gentle circulation of liquid growth medium present in said bioreactor when said bioreactor is in operation, said stainless steel sponge having a surface area and filament spacing sufficient to facilitate absorption of at least a portion of the gas stream into the liquid growth medium and to entrap or attach the cells within the sponge, yet maintain gentle circulation of the liquid medium.

2. The air lift bioreactor of claim 1, wherein the internal side walls in said growth chamber are configured to define an inwardly sloping conical section at the bottom of the growth chamber for directing liquid growth medium which is flowing down the internal side walls back towards the middle of said growth chamber where it can again be uplifted.

3. The air lift bioreactor of claim 2, further comprising a mixing chamber located beneath said chamber which is continuous with the middle of said growth chamber said mixing chamber including means for receiving the stream of gas to be bubbled up through the middle of said growth chamber.

4. The air lift bioreactor of claim 2, further comprising temperature control means for maintaining the liquid growth medium and the cells at a predetermined temperature within the growth chamber.

5. The air lift bioreactor of claim 4, further comprising gas stream supply means for supplying the gas stream to said bioreactor at a predetermined gentle flow rate.

6. The air lift bioreactor of claim 5, further comprising:
   a) liquid growth medium feed means for feeding liquid growth medium into said growth chamber at predetermined intervals and in predetermined quantities; and
   b) liquid growth medium removal means for removing liquid growth medium from said growth chamber at predetermined intervals and in predetermined quantities:
   whereby said air lift bioreactor may be continuously operated and biologocial products which are produced by the cells growing in said growth chamber can be harvested from liquid growth medium removed from said growth chamber.

7. The air lift bioreactor of claim 6, further comprising microprocessor control means for operating said temperature means, gas streams supply means, liquid growth medium feed means and liquid growth medium removal means according to predetermined operating instructions.

8. A bioreactor/fermentor which maintains cells or immobilized cells in suspension and whose geometry provides a mixing action to said cells with gentle aeration with a minimum of shear force, of the type comprising, a reactor vessel having a mixing chamber with a lower end and an open upper end, and a growth chamber with an open lower end of said mixing chamber and the open lower end of said growth chamber coincide with one another;

said mixing chamber having a first cylindrical side wall which defines the open upper end, a centrally located gas inlet means located in the lower end of said mixing chamber, and a bottom of the reactor vessel, for receiving the gas inlet means and, together with the first cylindrical side wall, for defining the lower end of said mixing chamber; and said growth chamber comprising a conical side wall defining the open lower end of said growth chamber, the conical side wall sloping inwardly toward the open upper end of said mixing chamber, a second cylindrical side wall of larger diameter than the first cylindrical side wall of said mixing chamber, the second cylindrical side wall being located above the conical side wall, and top lid means for providing an air tight seal on said growth chamber, the top lid means including gas vent means, whereby oxygen containing gas may be introduced into said reactor vessel through the centrally located gas inlet means and bubbled up through the cells and liquid medium to gently carry the cells and liquid medium upward from said mixing chamber to said growth chamber flow downward along the conical side wall sloping inwardly towards the open upper end of said mixing chamber to replace the cells and liquid medium being carried upwards from said mixing chamber by the oxygen containing gas, thereby providing a mixing action to said cells with aeration and a minimum of shear force while providing dissolved oxygen in the medium to support cell growth;

the improvement comprising a stainless steel wool filament like packing material means for increasing cell density by trapping cells and for providing a site for the attachment of anchorage dependent cells, said packing means being located in growth chamber of said bioreactor.

9. The bioreactor of claim 8 wherein said reactor vessel is supported within a temperature control jacket means having fluid inlet and fluid outlet means.

* * * * *